US008920513B2

(12) United States Patent
Rickner (10) Patent No.: US 8,920,513 B2
(45) Date of Patent: Dec. 30, 2014

(54) ANTI-REFLUXIVE AND TRIGONE SPARING INTERNAL URETERAL STENT

(76) Inventor: Thomas W. Rickner, Tulsa, OK (US)

( * ) Notice: Subject to any disclaimer, the term of this patent is extended or adjusted under 35 U.S.C. 154(b) by 105 days.

(21) Appl. No.: 12/870,133

(22) Filed: Aug. 27, 2010

(65) Prior Publication Data

US 2012/0053700 A1   Mar. 1, 2012

(51) Int. Cl.
*A61F 2/04*   (2013.01)
*A61M 27/00*   (2006.01)

(52) U.S. Cl.
CPC .................. *A61M 27/008* (2013.01)
USPC ...................................................... 623/23.66

(58) Field of Classification Search
CPC ......... A61M 5/00; A61M 27/008; A61F 2/04; A61F 2002/0048
USPC ................ 604/8–9; 623/23.64–23.7
See application file for complete search history.

(56) References Cited

U.S. PATENT DOCUMENTS

| | | | |
|---|---|---|---|
| 4,334,327 A | 6/1982 | Lyman | |
| 4,531,933 A * | 7/1985 | Norton et al. | 604/8 |
| 4,790,810 A | 12/1988 | Pugh, Jr. | |
| 5,019,102 A | 5/1991 | Hoene | |
| 5,380,270 A | 1/1995 | Ahmadzadeh | |
| 5,647,843 A | 7/1997 | Mesrobian | |
| 5,795,319 A | 8/1998 | Ali | |
| 5,984,965 A | 11/1999 | Knapp | |
| 6,066,113 A | 5/2000 | Overtoom | |
| 6,676,624 B2 | 1/2004 | Gellman | |
| 6,709,465 B2 * | 3/2004 | Mitchell et al. | 623/23.7 |
| 6,764,519 B2 | 7/2004 | Whitmore, III | |
| 6,908,447 B2 | 6/2005 | McWeeney | |
| 6,913,625 B2 | 7/2005 | Segura | |
| 6,945,950 B2 | 9/2005 | Clayman | |
| 6,991,614 B2 | 1/2006 | McWeeney | |
| 7,037,345 B2 * | 5/2006 | Bottcher et al. | 623/23.7 |
| 7,044,981 B2 | 5/2006 | Liu | |
| 7,316,663 B2 | 1/2008 | Whitmore, III | |
| 7,357,818 B2 | 4/2008 | Deal | |
| 7,396,366 B2 * | 7/2008 | Ward | 623/23.66 |
| 7,682,401 B2 * | 3/2010 | Deal | 623/23.66 |
| 8,057,461 B2 * | 11/2011 | Deal | 604/544 |
| 8,142,386 B2 * | 3/2012 | McWeeney | 604/9 |
| 8,252,065 B2 * | 8/2012 | Ward | 623/23.66 |
| 2003/0074082 A1 * | 4/2003 | Bottcher et al. | 623/23.7 |
| 2003/0163204 A1 | 8/2003 | Rix | |
| 2003/0199805 A1 * | 10/2003 | McWeeney | 604/8 |
| 2003/0199986 A1 * | 10/2003 | McWeeney et al. | 623/23.7 |
| 2004/0059279 A1 * | 3/2004 | McWeeney et al. | 604/8 |
| 2004/0143209 A1 | 7/2004 | Liu | |
| 2004/0181186 A1 | 9/2004 | Gellman | |
| 2004/0193092 A1 * | 9/2004 | Deal | 604/8 |
| 2005/0125072 A1 * | 6/2005 | Kolb | 623/23.7 |
| 2005/0149201 A1 * | 7/2005 | McWeeney et al. | 623/23.68 |

(Continued)

*Primary Examiner* — Andrew Iwamaye
(74) *Attorney, Agent, or Firm* — Yancy IP Law, PLLC (57) ABSTRACT

A ureteral stent has an elongated body connecting a coiled, renal segment to a coiled, bladder end segment. In one embodiment of the present invention, the coiled, bladder end segment and a lower, intramural segment of the elongated body are provided as a first flap and a second flap. The lower, intramural segment is of such length as to extend through a patient's intramural ureteral, preferably 2-4 cm. In another embodiment of the present invention, the coiled, renal segment is provided in a first plane and the coiled, bladder end segment is provided in a second plane such that the first plane and the second plane are transverse with respect to one another.

9 Claims, 6 Drawing Sheets

(56) References Cited

U.S. PATENT DOCUMENTS

| | | |
|---|---|---|
| 2005/0240280 A1 | 10/2005 | Aliski |
| 2005/0246038 A1 | 11/2005 | O'Keefe |
| 2006/0259151 A1* | 11/2006 | Ward .................... 623/23.7 |
| 2007/0032880 A1* | 2/2007 | Maeda .................... 623/23.7 |
| 2008/0086214 A1 | 4/2008 | Hardin |
| 2008/0249636 A1* | 10/2008 | Deal .................... 623/23.66 |
| 2008/0255679 A1* | 10/2008 | Ward .................... 623/23.66 |
| 2008/0288082 A1* | 11/2008 | Deal .................... 623/23.7 |
| 2009/0187254 A1* | 7/2009 | Deal et al. .................... 623/23.7 |
| 2010/0198359 A1* | 8/2010 | Ward .................... 623/23.66 |
| 2011/0320008 A1* | 12/2011 | Teague et al. .................... 623/23.65 |

\* cited by examiner

FIG. 11

ANTI-REFLUXIVE AND TRIGONE SPARING INTERNAL URETERAL STENT

BACKGROUND OF THE INVENTION

1. Field of the Invention

The present invention relates to internal ureteral stents.

2. Description of Related Art

Internal ureteral stents are generally used to assist movement of urine along a patient's ureter and into the patient's bladder in patients with ureteral obstructions or injury, or to protect the integrity of the ureter in a variety of surgical manipulations. Ureteral stents may be used to treat or avoid ureteral obstructions, such as ureteral stones or ureteral tumors, which disrupt the flow of urine from the kidneys to the bladder. Serious obstructions may cause urine to back up into the kidneys, threatening renal function.

Generally, ureteral stents are formed from a flexible material having sufficient resiliency to allow it to be straightened for insertion into the body passageway, while having sufficient memory to return to its predetermined retentive shape when in situ. Ureteral stents are positioned in the ureter by various procedures that are known to those of skill in the art including antegrade (percutaneous) placement, retrograde (cystoscopic) placement through the urethra, as well as by open ureterotomy or surgical placement in the ureter under direct visual placement. Ureteral stent positioning may be accomplished by several methods known to those of skill in the art.

Typical ureteral stents are tubular in shape, terminating in two opposing ends: a kidney (upper) end and a bladder (lower) end. The ends may be coiled to prevent the upward or downward migration of the stent. The kidney coil is designed to retain the stent within the renal pelvis of the kidney and to prevent stent migration down the ureter. The bladder coil sits in the bladder and is designed to prevent stent migration upwards toward the kidney. The bladder coil may also be used to aid in retrieval and removal of the stent. Currently, the upper and lower coiled ends of ureteral stents are offset by 180° and lie in substantially the same plane. Based on the anatomy of the kidney and bladder, this usually places the coiled, bladder end right on the trigone or just above it.

Ureteral stents, particularly the portion positioned in the ureter near the bladder and inside the bladder, may produce adverse effects including blood in the urine, a continual urge to urinate, and flank pain accompanying reflux of urine up the stent (e.g. when voiding) as pressure within the bladder is transmitted to the kidney. In short, stents may cause or contribute to significant patient discomfort and serious medical problems.

BRIEF SUMMARY OF THE INVENTION

The present invention generally relates to a ureteral stent having an elongated body connecting a coiled, renal segment to a coiled, bladder end segment. The coiled, renal segment is adapted to be received within a kidney. The coiled, bladder end segment is adapted to be received within a bladder.

In one embodiment of the present invention, the elongated body has an upper, tubular body that is connected to the coiled, renal segment and a lower, intramural segment that is connected to the coiled, bladder end segment such that the lower, intramural segment and coiled, bladder end segment are provided as a first flap and a second flap. The lower, intramural segment is of such length as to extend through a patient's intramural ureter, preferably 2-4 cm. One benefit of this configuration is the reduction and/or elimination of reflux of a patient's urine back into the ureter through the stent towards the kidneys.

In another embodiment of the present invention, the coiled, renal segment is provided in a first plane and the coiled, bladder end segment is provided in a second plane such that the first plane and the second plane are transverse with respect to one another. One benefit of this configuration is that the coiled, bladder end segment is positioned away from a patient's trigone which improves the comfort of the device to the patient.

BRIEF DESCRIPTION OF THE SEVERAL VIEWS OF THE DRAWINGS

The features and advantages of the present invention will become apparent from the following detailed description of a preferred embodiment thereof, taken in conjunction with the accompanying drawings, in which.

DETAILED DESCRIPTION OF THE INVENTION

Figure 1:
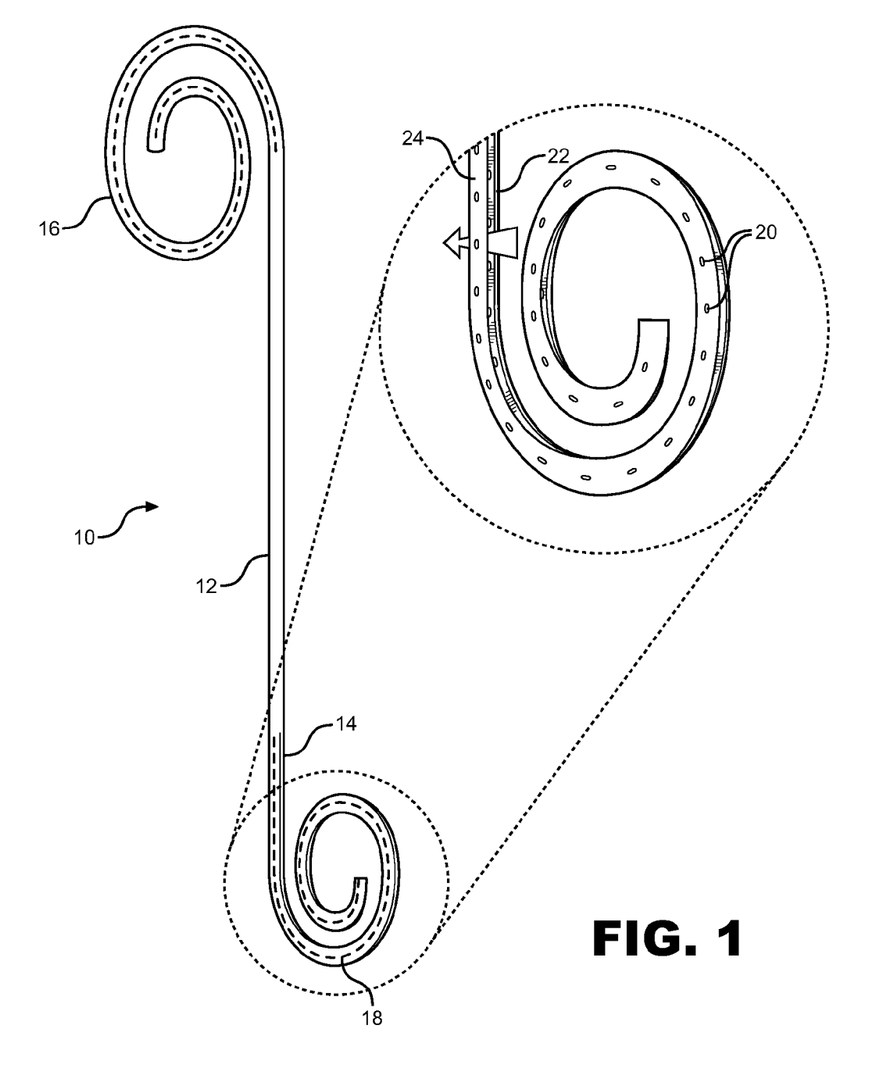
FIG. 1 shows a ureteral stent 10 with an enlarged coiled, bladder end segment 18 in accordance with one embodiment of the present invention.

FIG. 1 shows a ureteral stent 10 including an elongated body having a proximal end connected to a coiled, renal segment 16 and a distal end connected to a coiled, bladder end segment 18. The elongated body is designed to extend from the renal pelvis to the ureteral orifice. In a preferred embodiment, the elongated body has an upper, tubular body 12 that is connected to the coiled, renal segment at its proximal end and a lower, intramural segment 14 at its distal end that extends through the intramural ureter and connects to the coiled, bladder end segment 18. The upper, tubular body 12 has annular walls having an inner and outer diameter. The outer diameter of the upper, tubular body 12 may be substantially uniform throughout much of the length of the tube, or it may taper from a relatively short region of larger diameter (e.g. the site of repair, where there is a risk that the healing process will substantially restrict flow in the lumen) to a region of generally small diameter. The precise configuration may depend on the ureteral defect being corrected. The upper, tubular body 12 may also have openings extending through its walls; the openings may be arranged in various geometries (e.g. axial, circumferential, spiral). The coiled, renal segment 16 is adapted to be received within the kidney. The coiled, bladder end region 18 is adapted to be received within the bladder and the lower, intramural segment 14 of the stent is sized to match the intramural ureter. In one embodiment, the lower, intramural segment 14 is 2-4 cm in length. For illustrative purposes, coiled, renal segment 16 and coiled, bladder end segment 18 are shown as pigtail helical coils although any shape that will retain the ureteral stent 10 in place within the kidney and bladder will suffice. Coiled, bladder end segment 18 may include a plurality of openings 20 placed along its wall; the openings may be arranged in various geometries (e.g. axial, circumferential, spiral), but are not counter-posed.

The ureteral stent 10 may be derived from any number of biocompatible plastic materials. In one embodiment the ureteral stent 10 is formed from biocompatible plastic materials, including but not limited to polyester-based biocompatible polymers, nylon-based biocompatible polymers, polytetrafluoroethylene (PTFE) polymers, silicone polymers, polyurethane polymers, silicone polyurethane polymers, polyethylene polymers, and thermoplastic polymers, for example. In an embodiment in which it is necessary that the ureteral stent 10 undergo significant conformation changes, for example, during implantation, the ureteral stent 10 may be constructed from shape-memory material, such as PERCUFLEX® (Boston Scientific Corporation, Natick, Mass.), C-FLEX® (Xomed-Trease Inc.), FLEXIMA™, or other polymer material, for example. The ureteral stent 10 may have a hydrogel coating, which offers a further reduction of irritation due to contact of the stent 10 with tissue, or it may be embedded with antimicrobials or analgesics. The ureteral stent 10 may be made of a biodegradable polymer, for example, where it is desired that the stent 10 dissolve in-situ after its useful lifetime in the patient.

The ureteral stent 10 may also be produced in varying lengths and lumen diameters. The ureteral stent 10 is preferably designed to have a length of about 8 cm to about 30 cm and having outer diameters in the range of about 1 mm to about 4 mm. Most preferably, the outer diameter of the stent 10 according to the present invention range from about 1.5 mm to about 3 mm and most preferably the stent 10 will have a wall thickness in the range of about 0.25 mm to about 1 mm.

Figure 2:
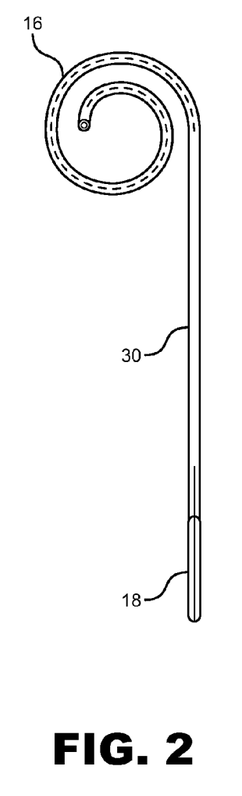
FIG. 2 shows a front, planar view of a right-sided ureteral stent 30 in accordance with one embodiment of the present invention.
Figure 3:
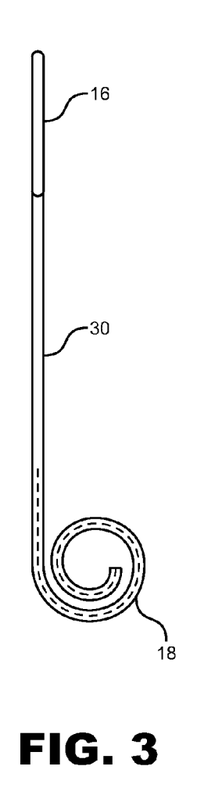
FIG. 3 shows a side, planar view of a right-sided ureteral stent 30 in accordance with one embodiment of the present invention.
Figure 4:
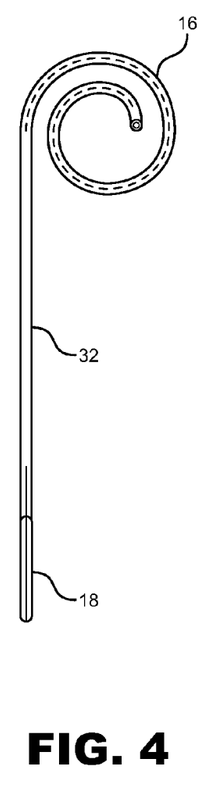
FIG. 4 shows a front, planar view of a left-sided ureteral stent 32 in accordance with one embodiment of the present invention.
Figure 5:
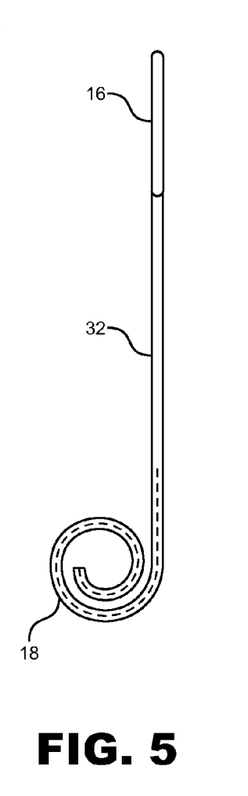
FIG. 5 shows a side, planar view of a left-sided ureteral stent 32 in accordance with one embodiment of the present invention.
Figure 6:
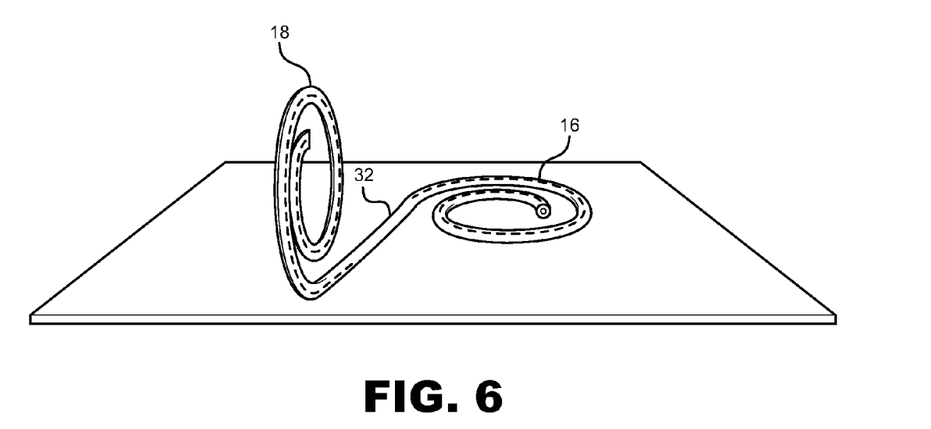
FIG. 6 shows a perspective view of a left-sided ureteral stent 32 in accordance with one embodiment of the present invention.
Figure 7:
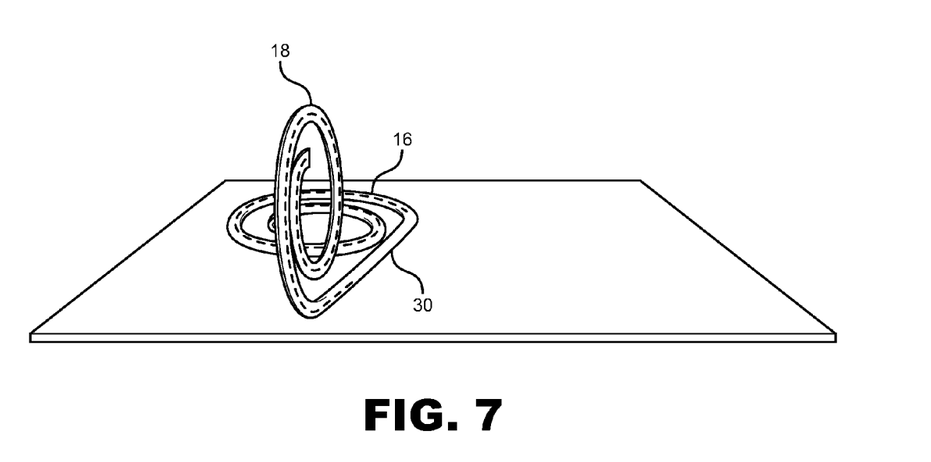
FIG. 7 shows a perspective view of a right-sided ureteral stent 30 in accordance with one embodiment of the present invention.
Figure 8:
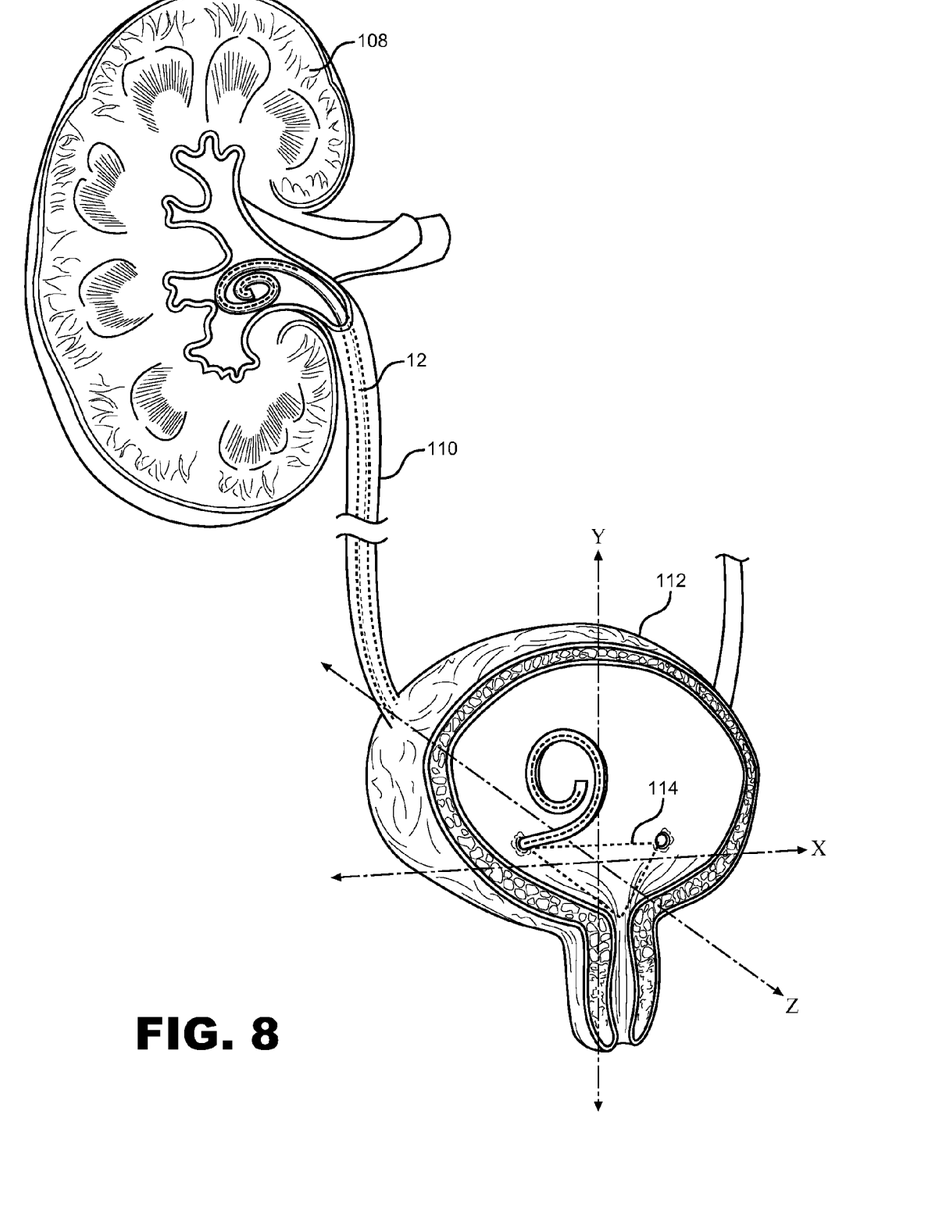
FIG. 8 shows the ureteral stent inserted within the kidney 108, ureter 110 and bladder 112 of a patient in accordance with one embodiment of the present invention.

FIGS. 2-7 show one embodiment of the present invention where the ureteral stent 10 may be configured as a right-sided ureteral stent 30 or a left-sided ureteral stent 32. One of skill in the art would understand that the use of the term "stent" or "ureteral stent" may be used to describe both the right-sided ureteral stent 30 and/or the left-sided ureteral stent 32. FIG. 2 and FIG. 3 show a right-sided ureteral stent 30 designed to be provided in the right kidney and right ureter of a patient. FIG. 4 and FIG. 5 show a left-sided ureteral stent 32 designed to be provided in the left kidney and left ureter. FIG. 6 shows the left-sided ureteral stent 32 having a coiled, renal segment 16 provided in a first plane and a coiled, bladder end segment 18 having only one coil provided in a second plane such that the first plane and the second plane are transverse with respect to one another. In the embodiment provided in FIG. 6, the first plane and the second plane are perpendicular with respect to one another. For example, the left-sided ureteral stent 32 has a coiled, renal segment 16 pointing to the left of the patient and the coiled, bladder end segment 18 pointed frontward. FIG. 7 shows the right-side ureteral stent 30 having a coiled, renal segment 16 provided in a first plane and a coiled, bladder end segment 18 having only one coil provided in a second plane such that the first plane and the second plane are transverse with respect to one another. In the embodiment provided in FIG. 7, the first plane and the second plane are perpendicular with respect to one another. For example, the right-side ureteral stent 30 has a coiled, renal segment 16 pointing to the right of the patient extending in a first plane and the coiled, bladder end segment 18 pointed toward the abdomen wall extending through a second plane positioned transverse to said first plane and anteriorly in relation to said first plane. As shown in FIG. 6 and FIG. 7, each of the right-sided ureteral stent 30 and the left-sided ureteral stent 32 include a coiled, renal segment extending from a proximal end of the elongated body, wherein said coiled, renal segment extends through a first plane (as shown in FIG. 8) extending laterally left or right from said elongated body such that the coiled, renal segment comprises a first coil that turns only in the first plane; and a coiled, bladder end segment extending from said distal end of said elongated body, wherein said coiled, bladder end segment extends through a second plane (as shown in FIG. 8) positioned transverse to said first plane and anteriorly in relation to said first plane such that the coiled, bladder end segment comprises a second coil that turns only in the second, wherein said first plane and said second plane are off-set from one another such that said coiled, bladder end segment is not thrown onto the trigone during use and wherein said coiled, bladder end segment has only one coil, preferably split. In the case where a patient has malrotated kidneys, the first plane and the second plane of the ureteral stent may be off-set from one another by less than 90° so that the bladder coil is not thrown onto the trigone.

FIG. 8 shows a right-sided ureteral stent 30 positioned within a patient in accordance with one embodiment of the present invention. One of ordinary skill in the art would understand how to position a right-sided ureteral stent 30 in a patient as provided herein. As indicated in FIG. 8, the coiled, renal segment 16 is positioned within the kidney 108, the elongated body is positioned within the ureter 110, and the coiled, bladder end segment 18 is positioned within the bladder 112. In accordance with one embodiment of the present invention, the coiled, bladder end segment 18 is positioned within the bladder 112 in such a manner that the coiled, bladder end segment 18 turns upward and off of the trigone 114 and bladder neck in accordance with one embodiment of the present invention. FIG. 8 illustrates the trigone 114 as a dashed triangle section provided near the bottom of the bladder. This configuration reduces the irritable voiding caused by irritation of the trigone 114 and the bladder neck.

Figure 9:
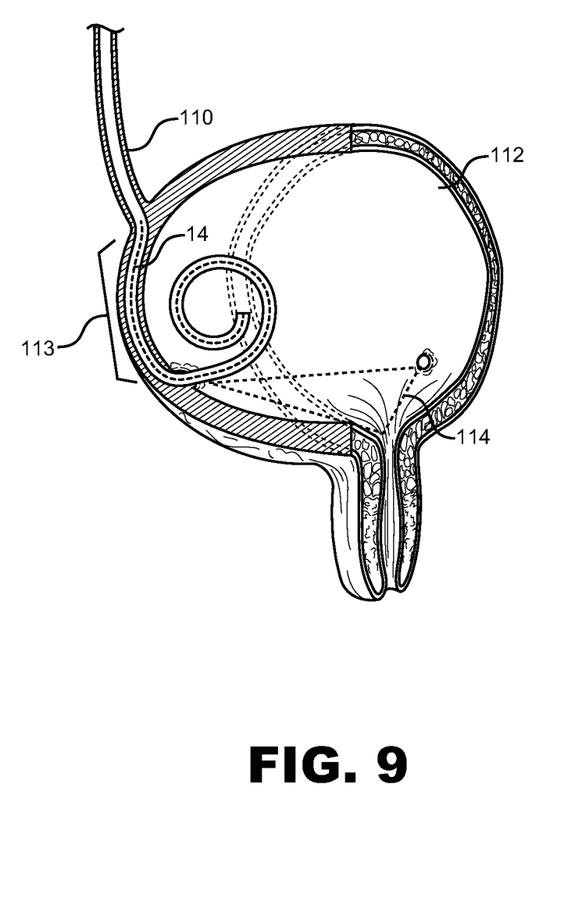
FIG. 9 shows the ureteral stent passing from the ureter 110, through the intramural ureter 113, and into the bladder 112 in accordance with one embodiment of the present invention.

FIG. 9 shows one embodiment of the present invention where the ureter stent 10 is placed in the ureter 110, through the intramural ureter 113, and into the bladder 112. In one embodiment, a lower, intramural segment 14 at the distal end of the elongated body extends through a patients intramural ureter 113. Preferably, the lower, intramural segment 14 extends approximately 2-4 cm through the intramural ureter 113. In a preferred embodiment, the lower, intramural segment 14 extends through the entire or substantially entire length of the intramural ureter 113. In this embodiment, the coiled, bladder end segment 18 and the lower, intramural segment 14 of the distal end of the elongated body are split to provide a first flap 22 and a second flap 24 as seen more clearly in FIG. 1. In a preferred embodiment, the beginning of the first flap 22 and second flap 24 are approximately 12-28 cm from the point of the beginning of the coil of the coiled, renal segment 16 located in the renal pelvis. The way it can be measured is to measure from the renal pelvis to the ureteral orifice (opening) in the bladder 112. This measurement may be done with a ureteral catheter either alone or over a guidewire. The flaps 22, 24 will extend backwards for 2-3 cm up toward the kidney 108 along with the associated openings 20 (as provided below), thus assuring that the beginning of the flaps 22, 24 are positioned within the intramural ureter 113. This can be easily measured at the time of implantation. Preferably, the first flap 22 and second flap 24 extend the entire length of the intramural ureter 113 and continue through the entire length of the coiled, bladder end segment 18. The first flap 22 and the second flap 24 are curved and coiled in the same direction adjacent to each other and each have a plurality of openings 20 such that an opening in the first flap 22 is offset from an opening in the second flap 24, thus preventing reflux when the flaps 22, 24 are coapted. In a preferred embodiment, the distal end of the coiled, bladder segment 18 is provided such that the flaps 22, 24 are fused together.

Figure 10:
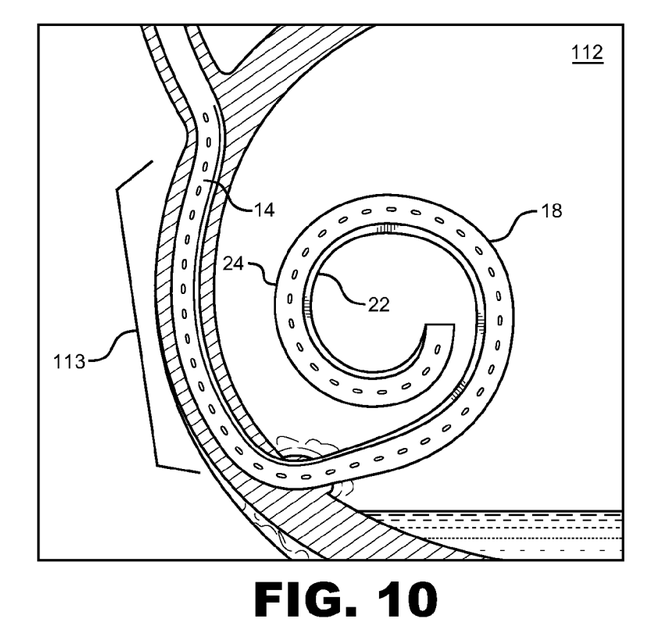
FIG. 10 shows an enlarged view of the ureteral stent passing through the intramural ureter 113 and into a non-full bladder in accordance with one embodiment of the present invention.
Figure 11:
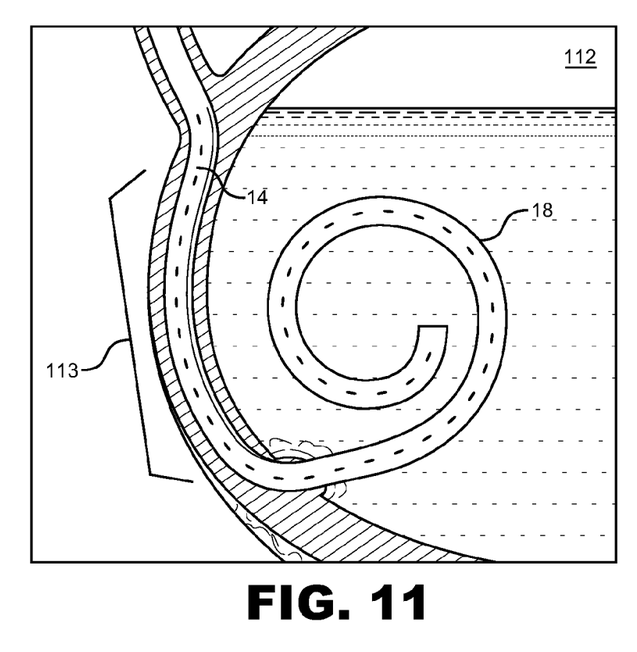
FIG. 11 shows an enlarged view of the ureteral stent passing through the intramural ureter 113 and into a substantially full bladder in accordance with one embodiment of the present invention.

As shown in FIG. 10, the lower, intramural segment 14 of the elongated body to the distal end of the coiled, bladder end segment 18 is split into a first flap 22 and a second flap 24 in accordance with one embodiment of the present invention. The flaps 22, 24 within the bladder 112 would have sufficient memory causing them to coil upward and adjacent to each other. The coiling should be of sufficient length to prevent migration backwards up the ureter 110. In one embodiment, the split may be such that the lower, intramural segment 14 and coiled, bladder end segment 18 are sliced open or into two half segments. In one embodiment, the lower, intramural segment 14 and the coiled, bladder end segment 18 may include a convex flap and a concave flap. It yet another embodiment, the first flap 22 and second flap 24 are flat. This will allow for easy coaptation of the two flaps 22, 24 created by the split to occur within the intramural ureter 113. In a preferred embodiment, the first flap 22 and the second flap 24 are flat as they extend through a patient's intramural ureter 113 just prior to the ureteral orifice. This distance that the flaps 22, 24 extend through the intramural ureteral 113 is preferably 2-4 cm. In this preferred embodiment, the first flap 22 and second flap 24 exit the ureteral orifice in an upward direction, e.g. 90°. In this preferred embodiment, when the flaps 22, 24 enter the bladder 112 the flaps 22, 24 would become semicircular with the first flap 22 of the coiled, bladder end segment 18 being convex so that a smooth surface and minimal surface area will be in contact with the bladder wall. In this embodiment, the second flap 24 of the coiled, bladder end segment 18 would also be convex in the same direction as the first flap 22 so that they fit against each other thus preventing reflux. In a preferred embodiment, the walls of the flaps 22, 24 would be much thinner than the walls of the elongated tubular body 12 of the ureteral stent 10. Thus, little pressure would be required to coapt the walls of the flaps 22, 24 together thus preventing reflux. The very nature of the intramural ureter 113 would provide coaptation of the lower, intramural segment 14 but the walls of the coiled, bladder end segment 18 would also coapt to assist in reducing reflux. This anti-refluxing mechanism preferably occurs within the ureteral stent 10 at a position within the intramural ureteral 113. This creates two flaps 22, 24 that travel through the intramural ureter 113, preferably in a flat configuration, and are thus easily coaptable. Their continuation into the bladder 112 using shape-memory of the material creates the coiled, bladder end segment 18 having flaps 22, 24 that are offset as provided previously. This configuration will cause less irritation within the bladder 112. Also as the flaps 22, 24 coil, they can become narrower toward the distal end and terminate as two very narrow flaps 22, 24. Alternatively, the flaps 22, 24 may be connected at the distal end of the coiled, bladder end segment 18. The coiled, bladder end segment 18 should be at least 5 cm long. This configuration should prevent reflux of urine up to the kidney 108 while also making it easy for the urine coming down from the kidney 108 to gain access to the bladder 112. The flaps 22, 24 preferably include a plurality of openings 20 that are offset on the two flaps 22, 24. As shown in FIG. 10, when the bladder 112 is not full, the plurality of openings 20 would be open. However, as shown in FIG. 13, when the bladder 112 is full, the pressure in the intramural ureteral 113 and bladder 112 pushed the two flaps 22, 24 together (i.e. coapts them) such that one cannot see completely through two offset openings 20. This configuration allows for better egress of urine down from the kidney 108 into the bladder 112. Additionally, it would prevent reflux back up the ureter 110. One advantage of having the stent 10 split into flaps 22, 24 and flat as it comes through the intramural ureter 113 is that this would make the lower, intramural segment 14 of the stent 10 and the coiled, bladder end segment 18 effectively smaller and thus reduce irritation resulting in less frequent voiding, less urgency to void, and less discomfort as one voids, all the result of the trigonal irritation.

As previously indicated, stents may be implanted or placed in the ureter by various techniques or procedures as are currently known and used. For example, a flexible guidewire is placed up the ureter 110 into the renal pelvis. After other procedures are performed, a ureteral catheter can be used to measure the distance from the renal pelvis to the ureteral orifice. This can actually be done at any time during the procedure. The stents will be identified by the diameter of the main body of the stent (5-8 FR) and the length is obtained by measuring the distance from the renal pelvis to the ureteral orifice. This allows the renal segment 16 to coil in the renal pelvis and the bladder end segment 18 to begin its coil in the bladder while the lower, intramural segment 14 of the elongated body is split and extends well into and, in fact, through the intramural ureter 113. This will occur if an accurate length is obtained. A second tube, referred to as a "pusher", may be used to push the stent 10 into position, including positioning the lower, intramural segment 14 of the stent 10 correctly within the intramural ureter 113. Such "pushers" are generally known in the art and may be adapted by one of skill in the art such that it may be used to correctly position the lower, intramural segment 14 of the stent 10 within the intramural ureter 113.

Although the present invention has been disclosed in terms of a preferred embodiment, it will be understood that numerous additional modifications and variations could be made thereto without departing from the scope of the invention as defined by the following claims.

What is claimed is:

1. A ureteral stent for facilitating drainage from a kidney to a bladder of a patient, comprising:
   an elongated body including a length sufficient to extend within a ureter from the kidney to the bladder, said elongated body having a proximal end and a distal end, said elongated body having a longitudinal axis extending from the proximal end to the distal end;
   a coiled, renal segment extending from said proximal end of said elongated body, wherein said coiled, renal segment extends through a first plane extending laterally left or right from said elongated body such that the coiled, renal segment comprises a first coil that turns only in the first plane;

a coiled, bladder end segment extending from said distal end of said elongated body, wherein said coiled, bladder end segment extends through a second plane positioned substantially perpendicular to said first plane, wherein said coiled, bladder end segment is positioned anteriorly in relation to said first plane, wherein the coiled, bladder end segment comprises a second coil that turns only in the second plane, wherein said first plane and said second plane are off-set from one another such that said coiled, bladder end segment is not thrown onto the trigone during use and wherein said coiled, bladder end segment has only one coil that coils towards the proximal end; and wherein the first coil coils around a first coil axis and the second coil coils around a second coil axis, wherein the first coil axis and the second coil axis are not parallel to the longitudinal axis.

2. The ureteral stent of claim 1, wherein said coiled, renal segment and said coiled, bladder end segment are formed from shape-memory material.

3. The ureteral stent of claim 1, wherein said elongated body has an upper, tubular body connected to said coiled, renal segment and a lower, intramural segment connected to said coiled, bladder end segment.

4. The ureteral stent of claim 3, wherein said lower, intramural segment is 2-4 cm in length.

5. A ureteral stent for facilitating drainage from a kidney to a bladder of a patient, comprising:

an elongated body including a length sufficient to extend within a ureter from the kidney to the bladder, said elongated body having an upper, tubular body provided at a proximal end and a lower, intramural segment provided at a distal end;

a coiled, renal segment extending from said proximal end of said elongated body; and a coiled, bladder end segment extending from said lower, intramural segment provided at the distal end of said elongated body;

said intramural segment and said coiled, bladder segment having a longitudinal axis and an outer diameter;

wherein said coiled, bladder end segment and said lower, intramural segment consist of two half segments forming a first flap and a second flap such that said first flap and said second flap are parallel to each other and are curved and coiled in the same direction adjacent to each other;

wherein said first flap and said second flap are uncoupled to each other at least along a portion of their length due to a slit extending through said intramural segment and said coiled, bladder segment, the slit having a width traversing the entire outer diameter of said intramural segment and said coiled, bladder segment.

6. The ureteral stent of claim 5, wherein said lower, intramural segment is of such length as to extend entirely through a patient's intramural ureter.

7. The ureteral stent of claim 5, wherein said first flap and said second flap are flat flaps or flat with a convex shape.

8. The ureteral stent of claim 5, wherein said first flap and said second flap each have a plurality of openings such that an opening in said first flap is offset from an opening in said second flap.

9. The ureteral stent of claim 5, wherein said first flap and said second flap extend the entire length of the coiled, bladder end segment.

* * * * *